United States Patent [19]

Yamazato et al.

[11] Patent Number: 4,503,156

[45] Date of Patent: Mar. 5, 1985

[54] REAGENT MIXTURE FOR MEASURING MAGNESIUM

[75] Inventors: Fujio Yamazato, Tokyo; Kuniaki Tokuda, Kawagoe; Toshihiko Oda, Kyoto, all of Japan

[73] Assignee: Wako Pure Chemical Industries, Ltd., Osaka, Japan

[21] Appl. No.: 424,180

[22] Filed: Sep. 27, 1982

[30] Foreign Application Priority Data

Sep. 28, 1981 [JP] Japan .................................. 56-153329

[51] Int. Cl.$^3$ ...................... G01N 21/78; G01N 33/52
[52] U.S. Cl. .......................................... 436/79; 436/74
[58] Field of Search ............................ 436/74, 79, 164

[56] References Cited

U.S. PATENT DOCUMENTS 3,754,865  8/1973  Gindler ............................ 436/74 X
4,220,451  9/1980  Stefanchik ......................... 436/105
4,308,027  12/1981 Ceriotti ............................ 436/74

OTHER PUBLICATIONS

Watanabe et al., Chemical Abstracts, vol. 88, 1978, No. 88:163269a.
Fried et al., Chemical Abstracts, vol. 88, 1978, No. 88:132928k.
Tanaka et al., Chemical Abstracts, vol. 89, 1978, No. 89:70227r.
Gonalez et al., Chemical Abstracts, vol. 95, 1981, No. 95:107838t.

*Primary Examiner*—Arnold Turk
*Attorney, Agent, or Firm*—Armstrong, Nikaido, Marmelstein & Kubovcik

[57] ABSTRACT

A reagent mixture for measuring magnesium comprising Xylylazo Violet I or II as a color producing agent and at least one of sulfide compounds and thioureide compounds, and if necessary one or more surface active agents, can be stored for a long period of time stably and can give a stable color development.

9 Claims, No Drawings

REAGENT MIXTURE FOR MEASURING MAGNESIUM

This invention relates to a stabilized reagent mixture for measuring magnesium.

Magnesium is the fourth largest cation among various cations widely distributed in a living body. In a cellular liquid, magnesium is the second largest cation next to potassium and has an intimate relation to activities of many enzymes. In an extracellular liquid, magnesium is distributed in amount next to sodium, potassium, and calcium and relates to an excitation of nerves and muscles. Particularly, the amount of magnesium has a relation with that of calcium, which correlation gives important actions for a living body.

The presence of magnesium in a living body was proved by Holmes in 1858 for the first time. But since suitable measuring methods for magnesium have been established only recently and appearance of clinical symptoms peculiar to matabolic abnormal of magnesium has been rare, the importance of the magnesium in a living body was not recognized until recently and little attention was directed to the magnesium. With a recent development of atomic-absorption spectroscopy, it becomes possible to measure the amount of magnesium precisely and rapidly with a small amount of sample, which results in developing the study of metabolism of magnesium. At present, fundamental study on magnesium in a living body is considerably developing and the measurement of magnesium is going to be employed in daily examinations in clinical examinations. For example, there are known, as low magnesium content blood diseases, chronic alcoholism, epilepsy, congestive heart failure, hyperthyroidism, rickets, uremia, etc.; as high magnesium content blood diseases, hypertrophic arthritis, atherosclerosis, essential hypertension, insufficiency of kidney function, etc. The measurement of magnesium is going to be applied to diagnosis of these diseases.

As measuring methods for magnesium, there are mainly employed an atomic-absorption spectroscopy and a colorimetric method using Xylylazo Violet (also called as Xylydyl Blue or Magon). As to the atomic-absorption spectroscopy, there is no problem in accuracy and the necessary sample amount for measuring, but this method is not suitable for measuring a large number of samples for many test items at one time, such a testing system being employed for clinical examinations. On the other hand, in the colorimetric method using Xylylazo Violet which is a colorimetric reagent for alkaline earth metals, this color producing reagent is a blue dye usually having the maximum absorption at near 600 nm in an alkaline state. But when a chelate is formed from this color producing reagent together with an alkaline earth metal, the maximum absorption transfers to near 515 nm. Since calcium shows a similar color development in the measurement of an increase of absorbance at 515 nm, glycoletherdiamine-N,N,N',N'-tetraacetic acid (GEDTA) is usually used as a masking agent for calcium. This colorimetric method is excellent in sensitivity and high in both accuracy and reliability, so that this method is going to be employed widely but also has some defects. The first defect is that the stability of this color producing reagent at near pH 11 which is most preferable pH for color development is very bad. The second defect is that this color producing reagent is hardly dissolved in water at neutral or acidic side wherein its stability is maintained, although the solubility at alkaline side is relatively good. This tendency is not improved even if a sulfonic acid group is introduced into the molecule of this color producing reagent (that having a sodium sulfonate group being called Xylylazo Violet I and that having no sulfonic acid group being called Xylylazo Violet II). The third defect is that the wavelength shift to lower wavelength side is as relatively small as usually about 85 nm (600 nm→515 nm) when a chelate is produced from this color producing reagent and magnesium. Therefore, when the color producing reagent is added so as to maintain the linearity of the calibration curve in the clinically necessary range, the reagent blank necessarily increases, for example, the absorbance at 515 nm is decreased to about 0.7, which results in lowering in reliability considering the accuracy of spectrophotometer.

Thus, in order to improve the dissolution of the color producing reagent, the stability under alkaline state, the lowering in absorbance of the color producing reagent at the measuring wavelength of near 515 nm (the shift of $\lambda_{max}$ of the color producing reagent to longer wavelength side) and sensitivity, it was usual to use an organic solvent such as methanol, ethanol, propanol, ethylene glycol, ethylene glycol monomethyl ether, or the like in an amount of 30 to 70% by volume. But the use of the organic solvent is unpreferable not only from the viewpoint of safety and hygiene of workers but also from the defects of damaging tubes, change-over valves, and plastic-made cells, when an automatic analyzer is used or from the viewpoint of insufficiency in stabilizing action of the color producing reagent under alkaline conditions.

It is an object of this invention to provide a reagent mixture for measuring magnesium overcoming the defects mentioned above.

This invention provides a reagent mixture for measuring magnesium which comprises a color producing reagent of the formula:

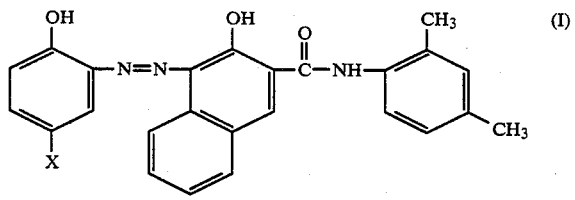

wherein X is SO$_3$H, SO$_3$Na or H; and as a stabilizer for the color producing reagent, at least one of sulfide compounds and thioureide compounds is used; and if necessary, a surface active agent as an auxiliary agent is used for dissolving (solubilizing agent) the color producing reagent.

The color producing reagent of the formula (I) wherein X is SO$_3$Na is called Xylylazo Violet I (3-hydroxy-4-(2-hydroxy-5-sulfophenylazo)-2',4'-dimethyl-2-naphthanilide Na salt) and wherein X is H is called Xylylazo Violet II (3-hydroxy-4-(2-hydroxyphenylazo)-2',4'-dimethyl-2-naphthanilide).

In the case of dissolving the color producing reagent of the formula (I) in an aqueous solution, there can effectively be used cationic, nonionic and amphoteric surface active agents when the aqueous solution is acidic or neutral, and in the case of dissolving rapidly in an alkaline aqueous solution (the color producing agent of the formula (I) being able to be dissolved naturally if standing for a long period of time), there can effectively be used nonionic, amphoteric and anion surface active agents. These effects are remarkably exhibited when there is used Xylylazo Violet I wherein a sulfonic acid group is introduced. But the same or higher ability for shifting the absorption of the color producing reagent itself to longer wavelength side as in the case of using an organic solvent and the sensitizing action for magnesium in order to increase to about 50% can only be obtained when nonionic or amphoteric surface active agents are used.

Dissolution of hardly soluble substances by using a surface active agent has often been applied to clinical diagnostic reagents, but the use of such a surface active agent for shifting the absorption of the color producing reagent to longer wavelength side, for lowering the reagent blank value at the measuring wavelength and for improving sensitization has not been known in this art.

As the nonionic surface active agent, there can be used conventional ones, for example, polyoxyethylene alkyl ethers, polyoxyethylene alkyl esters, polyoxyethylene alkylamines, polyoxyethylene alkylamides, sorbitan alkyl esters, polyoxyethylene sorbitan alkyl esters, etc.

As the amphoteric surface active agent, there can be used conventional ones. Among them, alkyl betaine series are particularly effective.

These surface active agents can be used alone or as a mixture thereof. Further, these surface active agents can be used together with one or more anionic surface active agents.

The effective concentration of the surface active agent in the reagent mixture is usually 0.05 to 20.0% by wt/vol.

Table I shows dissolving power of individual surface active agents, maximum absorption wavelengths of the color producing reagent after dissolution, absorbances at the measuring wavelength (near 515 nm) and sensitivities of standard magnesium (5 mg/dl).

TABLE 1

| | Organic solvents or surface active agents | | Solubility*1 XV-I Acidic | Solubility*1 XV-I Neutral | Solubility*1 XV-I Alkaline | Solubility*1 XV-II Acidic | Solubility*1 XV-II Neutral | Solubility*1 XV-II Alkaline | Color producing reagent Maximum absorption wavelength (nm) | Color producing reagent Absorbance (520 nm) | Maximum absorption wavelength of color producing reagent and magnesium chelate (nm) | Sensitivity*2 |
|---|---|---|---|---|---|---|---|---|---|---|---|---|
| Organic solvent (comparison) | None | — | x | x | Δ | x | x | Δ | 562 | 0.863 | 510 | 0.205 |
| | | vol % | | | | | | | | | | |
| | Ethanol | 50 | Δ | Δ | o | x | Δ | o | 600 | 0.675 | 513 | 0.302 |
| | Isopropyl alcohol | 50 | Δ | Δ | o | x | Δ | o | 584 | 0.670 | 514 | 0.298 |
| | Ethylene glycol | 50 | Δ | o | o | Δ | Δ | o | 605 | 0.635 | 515 | 0.295 |
| | Ethyl Cellosolve | 50 | Δ | o | o | Δ | Δ | o | 612 | 0.610 | 515 | 0.293 |
| Surface active agent | | wt./vol % | | | | | | | | | | |
| Nonionic | Polyoxyethylene isooctyl ether | 1 | o | o | o | x | Δ | o | 612 | 0.650 | 516 | 0.292 |
| | Polyoxyethylene lauryl ether | 1 | o | o | o | x | Δ | o | 610 | 0.624 | 515 | 0.290 |
| | Polyoxyethylene sorbitan monolaurate | 1 | o | o | o | x | Δ | o | 616 | 0.592 | 514 | 0.280 |
| | Polyoxyethylene sorbitan triacetate | 1 | o | o | o | x | Δ | o | 618 | 0.600 | 516 | 0.292 |
| | Polyoxyethylene laurylamine | 1 | o | o | o | x | Δ | o | 620 | 0.610 | 514 | 0.288 |
| Cationic | Cetyltrimethyl ammonium bromide | 0.3 | o | o | o | Δ | Δ | Δ | Absorption curve is deformed. | | | |
| | Zephiramine | 0.3 | o | o | o | x | Δ | Δ | Absorption curve is deformed. | | | |
| Anionic | Sodium laurylbenzene sulfonate | 1 | x | x | o | x | x | o | 560 | 1.037 | 510 | 0.188 |
| | Sodium polyoxyethylene laurylphenyl sulfonate | 1 | x | x | o | x | x | o | 566 | 0.844 | 510 | 0.158 |
| Ampho- | Lauryl betaine | 1 | Δ | o | o | x | Δ | o | 622 | 0.617 | 518 | 0.298 |

TABLE 1-continued

| | Solubility[*1] | | | | | | Color producing reagent | Maximum absorption wavelength of color | |
| --- | --- | --- | --- | --- | --- | --- | --- | --- | --- |
| | XV-I | | | XV-II | | | Maximum absorption wave- | Absorb- | producing reagent and magnesium |
| Organic solvents or surface active agents | Acidic | Neutral | Alkaline | Acidic | Neutral | Alkaline | length (nm) | ance (520 nm) | chelate (nm) | Sensitivity[*2] |
| teric | | | | | | | | | | |

Note to Table (1)
[*1]XV-I: Xylylazo Violet I
XV-II: Xylylazo Violet II
Acidic: pH 5 with HCl
Neutral: pH 7 with 0.01M tris-hydrochloric acid buffer solution
Alkaline: pH 11 with 0.01M sodium carbonate
Dissolution of color producing reagent in an amount of 5 mg/dl with the following evaluation:
o: within 5 minutes
Δ: within 24 hours
x: more than 24 hours or insoluble
[*2]After adding 3 ml of color producing reagent solution to 20 μl of magnesium standard solution (Mg, 5 mg/dl) and mixing, the resulting mixture was allowed to stand for 5 minutes, followed by measurement of each absorbance at the maximum absorption wavelength of the color producing reagent and magnesium chelate shown in Table 1 in contrast to the blank.

Deterioration of the color producing reagent of the formula (I) mainly under alkaline conditions seems to be caused by increasing of blank value at initial stage followed by lowering in sensitivity, which results in proceeding the following deterioration reaction:

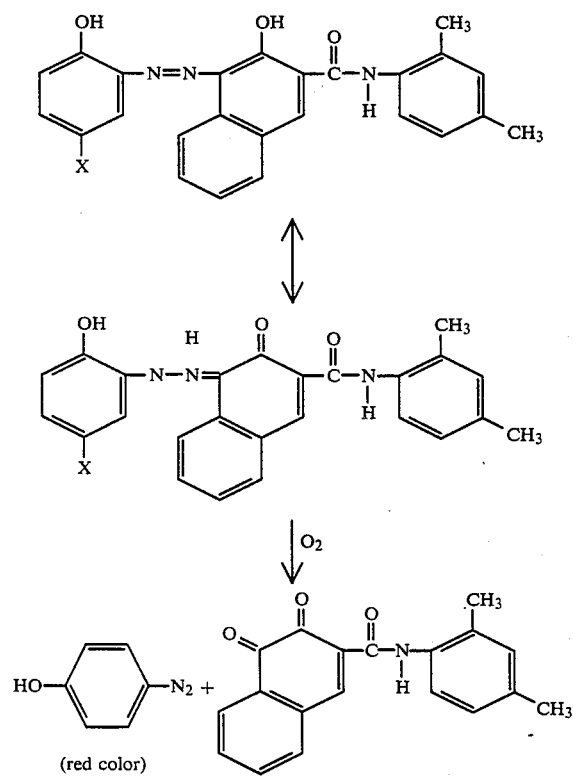

But to this deterioration reaction, a usual stabilizer such as BHA (3(2)-t-butyl-4-hydroxyanisole), BHT (3(2)-t-butyl-4-hydroxytoluene), DABCO (1,4-diazabicyclo[2,2,2]octane), or the like sometimes shows a little effect in the presence of an organic solvent but does not show any effect in an alkaline aqueous solution. But, it is a very surprising thing that a sulfide compound or a thioureide compound shows a remarkable effect on stabilizing the color producing reagent solution in a pH range of about 1 to 12 irrespective of the presence of an organic solvent.

As the sulfide compound, water soluble monosulfides represented by the formula:

$$Y-Z-S-Z-Y \qquad (II)$$

wherein Z is an alkylene group having preferably 1 to 5 carbon atoms or a phenylene group; and Y is a water soluble substituent such as OH, COOH, or $NH_2$, are preferable. Preferable examples of monosulfides are β-thiodiglycol, thiodiglycolic acid, 3,3'-thiodipropionic acid, thiodiphenylamine, etc.

As the thioureide compound, thioreide derivatives represented by the formula:

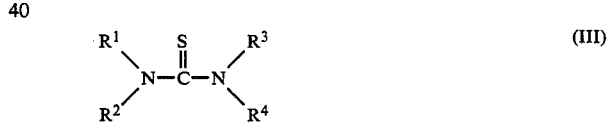

wherein $R^1$ to $R^4$ are independently hydrogen, a lower alkyl group preferably having 1 to 5 carbon atoms or a phenyl group, are preferable. Preferable examples of thioureide compounds are thiourea, methylthiourea, phenylthiourea, etc.

These stabilizers can be used alone or as a mixture thereof. The amount of the stabilizer in the reagent mixture is usually 0.005 to 2% by wt/vol.

These stabilizers show the excellent effect not only in an acidic or neutral aqueous solution wherein the color producing reagent is relatively stable or in an organic solvent but also in an alkaline solution even near pH 11 at which the measuring is conducted. The stabilized reagent mixture using such a stabilizer can be maintained at 40° C. for at least 2 years without any change.

Even if there are used sulfur-containing compounds other than the sulfide compounds and thioureide compounds mentioned above such as mercaptanes containing a thiol group (a SH group) having reducing force, e.g., mercaptoethanol, thioglycolic acid, etc.; inorganic sulfur-containing compounds, e.g., sulfites, metabisulfites, thiosulfates, hydrosulfites, etc., no such an effect of the use of the sulfide and thioureide compounds can be obtained. This is a very unexpected thing. The effect of these stabilizers is shown in Tables 2 and 3.

TABLE 2

| Base<br>Dissolving agent | | Sodium carbonate (0.1M)<br>Ethanol (50% vol) | | | | | | |
|---|---|---|---|---|---|---|---|---|
| Stabilizer | Kind | — | Thiodi-<br>phenylamine | Phenyl-<br>thiourea | Sodium<br>sulfite | BHT | BHA | DABCO |
| | Amount wt/vol % | — | 0.01 | 0.1 | 0.1 | 0.1 | 0.1 | 0.1 |
| Blank | 40° C., 1 week | 170% | 100% | 98% | 128% | 165% | 172% | 106% |
| | 40° C., 1 year | — | 101% | 96% | — | — | — | — |
| Degree of color | 40° C., 1 week | 34% | 100% | 100% | 58% | 34% | 36% | 94% |
| development | 40° C., 1 year | — | 102% | 105% | — | — | — | — |
| Measured value | 40° C., 1 week | 1.4 | 2.2 | 2.1 | 1.5 | 1.5 | 1.4 | 2.1 |
| (mg/dl) | 40° C., 1 year | — | 2.1 | 2.1 | — | — | — | — |

TABLE 3

| Base<br>Dissolving agent | | Sodium carbonate (0.1M)<br>Polyoxyethylene isooctyl ether (1% vol) | | | | | | | | |
|---|---|---|---|---|---|---|---|---|---|---|
| Stabilizer | Kind | — | β-Thio-<br>glycol | Thiodi-<br>glycolic<br>acid | 3,3'-Thiodi-<br>propionic<br>acid | Thiourea | β-Thiodi-<br>glycol | Thio-<br>glycolic<br>acid | Sodium<br>thiosulfate | DABCO |
| | Amount,<br>wt/vol % | — | 0.1 | 0.1 | 0.1 | 0.1 | 0.1 | 0.1 | 0.1 | 0.1 |
| | Kind | — | — | — | — | — | Methyl-<br>thiourea | — | — | — |
| | Amount,<br>wt/vol % | — | — | — | — | — | 0.1 | — | — | — |
| Blank | 40° C., 1 week | 123% | 104% | 99% | 98% | 100% | 99% | 129% | 122% | 125% |
| | 40° C., 1 year | — | 101% | 100% | 102% | 98% | 98% | — | — | — |
| Degree of color | 40° C., 1 week | 60% | 100% | 101% | 102% | 101% | 103% | 55% | 63% | 77% |
| development | 40° C., 1 year | — | 96% | 98% | 100% | 99% | 98% | — | — | — |
| Measured value | 40° C., 1 week | 1.6 | 2.3 | 2.1 | 2.1 | 2.2 | 2.3 | 1.5 | 1.7 | 1.8 |
| (mg/dl) | 40° C., 1 year | — | 2.2 | 2.2 | 2.2 | 2.3 | 2.2 | — | — | — |

Note to Tables 2 and 3
[1]Blank:

$$\frac{\text{Absorbance at 520 nm in contrast to water after standing at 40° C. for 1 week or 1 year}}{\text{Absorbance at 520 nm in contrast to water at the day of preparing the color producing reagent solution}} \times 100(\%)$$

[2]Degree of color development:
After adding 3 ml of color producing reagent solution to 20 μl of magnesium standard solution (Mg 5 mg/dl) and mixing, the resulting mixture was allowed to stand for 5 minutes, followed by measurement of each absorbance at 520 nm in contrast to the blank.
[3]Measured value:
To 20 μl of serum, 3 ml of color producing reagent solution was added and mixed, and the resulting mixture was allowed to stand for 5 minutes. Then, absorbance of the resulting mixture at 520 nm was measured in contrast to the blank. Magnesium concentration was obtained from the calibration curve.

Magnesium concentration in the same serum by a    40° C., 1 week 2.2
newly prepared color producing reagent solution (mg/dl)    40° C., 1 year 2.2

On the other hand, since these stabilizers of the formulae (II) and (III) show the stabilizing effect for the color producing reagent and for the color development, when the stabilizers of formulae (II) and (III) are used, the color development of the standard and serum is stabilized. Therefore, no change of developed color can be admitted at least for 3 days.

The reagent mixture of this invention comprising the color producing reagent of the formula (I), a stabilizer of the formula (II) or (III) and/or a surface active agent may further contain one or more conventionally used alkalifying agents, buffering agents such as alkali metal hydroxides, carbonates, borates, monoethanolamine, diethanolamine, triethanolamine, trishydroxymethylaminomethane, etc., masking agents for calcium such as GEDTA, etc.

This invention is illustrated by way of the following Examples.

EXAMPLE 1

Color Producing Reagent Solution A

| Cetyltrimethylammonium chloride | 0.1 g |
|---|---|
| Tween 80 (polyoxyethylene sorbitan monooleate, nonionic surface active agent) | 1.0 g |
| Xylylazo Violet I | 0.01 g |

These ingredients were dissolved in distilled water to make the volume 100 ml. The pH of the solution was adjusted to 5 by HCl.

Color Producing Reagent Solution B

| Anhydrous sodium carbonate | 2.16 g |
|---|---|
| GEDTA | 0.003 g |

Use Example 1

Equal amounts of color producing reagent solutions A and B were mixed to give a color producing reagent solution. To 20 μl of a sample, 3 ml of the resulting color producing reagent solution was added and allowed to stand at room temperature for 5 minutes. Absorbance at 515 nm was read on and was compared with the calibration curve to give the magnesium concentration in the sample.

EXAMPLE 2

| Xylylazo Violet II | 0.005 g |
|---|---|
| Phenylthiourea | 0.1 g |
| GEDTA | 0.002 g |
| Anhydrous potassium carbonate | 1.06 g |

| | |
|---|---|
| -continued | |
| Ethanol | 50 ml |

The above-mentioned ingredients were added to distilled water to make the volume 100 ml.

The resulting color producing reagent solution was stable for at least 2 years.

EXAMPLE 3

| | |
|---|---|
| Xylylazo Violet I | 0.005 g |
| Brij 35 (polyoxyethylene lauryl ether, nonionic surface active agent) | 1 g |
| Triethanolamine | 2 g |
| Sodium carbonate | 1.06 g |
| GEDTA | 0.003 g |
| Methylthiourea | 0.1 g |
| β-Thiodiglycol | 0.1 g |

The above-mentioned ingredients were added to distilled water to make the volume 100 ml.

The resulting color producing reagent solution was effective at least 3 years without causing any undesirable change.

What is claimed is:

1. In a reagent mixture for measuring magnesium containing a color producing reagent of the formula:

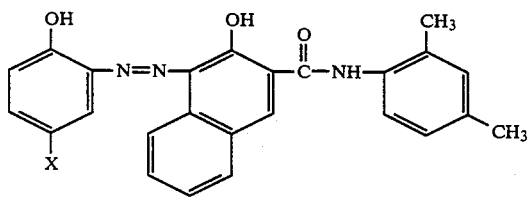

wherein X is SO$_3$H, SO$_3$Na or H, the improvement wherein the reagent mixture includes a stabilizer for the color producing reagent of at least one of sulfide compounds and thioureide compounds in an effective amount to stabilize the color producing reagent.

2. A reagent mixture according to claim 1, wherein the stabilizer is a sulfide compound.

3. A reagent mixture according to claim 2, wherein the sulfide compound is a water soluble monosulfide compound.

4. A reagent mixture according to claim 3, wherein the water soluble monosulfide compound is represented by the formula:

$$Y-Z-S-Z-Y$$

wherein Z is an alkylene group or a phenylene group; and Y is a water soluble substituent.

5. A reagent mixture according to claim 1, wherein the stabilizer is a thioureide compound.

6. A reagent mixture according to claim 5, wherein the thioureide compound is a thioureide derivative of the formula:

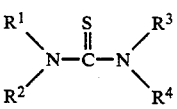

wherein $R^1$, $R^2$, $R^3$ and $R^4$ are independently hydrogen, a lower alkyl group or a phenyl group.

7. A reagent mixture according to claim 1, wherein the stabilizer is at least one member selected from the group consisting of β-thiodiglycol, thiodiglycolic acid, 3,3'-thiodipropionic acid, thiodiphenylamine, thiourea, methylthiourea and phenylthiourea.

8. A reagent mixture according to claim 1, which further comprises at least one surface active agent.

9. A reagent mixture according to claim 8, wherein the surface active agent is selected from the group consisting of nonionic and amphoteric surface active agents.

* * * * *